United States Patent [19]
Nabai et al.

[11] Patent Number: 5,483,972
[45] Date of Patent: Jan. 16, 1996

[54] BIOPSY WOUND CLOSURE DEVICE

[76] Inventors: Hossein Nabai, 14555 Levan Rd., Ste. 410, Livonia, Mich. 48154; Homayoon Rahbari, 1314 N. Macomb St., P.O. Box 360, Monroe, Mich. 48161

[21] Appl. No.: 358,820

[22] Filed: Dec. 19, 1994

Related U.S. Application Data

[62] Division of Ser. No. 56,399, May 4, 1993, Pat. No. 5,388,588.

[51] Int. Cl.⁶ .................................................... A61B 10/00
[52] U.S. Cl. .................................................. 128/749; 604/15
[58] Field of Search ........................... 128/749, 753, 128/754, 759; 604/1, 11, 14, 15, 18; 606/108, 167, 170, 184, 185

[56] References Cited

U.S. PATENT DOCUMENTS

| | | | |
|---|---|---|---|
| 3,712,296 | 1/1973 | Gradone | 128/759 |
| 3,739,781 | 6/1973 | Patel | 604/11 |
| 3,877,464 | 4/1975 | Vermes | 128/759 |
| 3,995,618 | 12/1976 | Kingsley et al. | 128/759 |
| 4,235,244 | 11/1980 | Abele et al. | 128/759 |
| 5,007,895 | 4/1991 | Burnett | 604/13 |
| 5,275,616 | 1/1994 | Fowler | 601/15 |

*Primary Examiner*—Max Hindenberg
*Attorney, Agent, or Firm*—Alex Rhodes

[57] ABSTRACT

A closure device for performing a routine biopsy procedure without the use of sutures or butterfly bandages. The method and closure device controls bleeding, repairs the biopsy site, reduces the likelihood of inducing excessive scarring and reduces the handling of tissue. The closure device is comprised of a circular sponge made from an absorbable foam material which swells and fills up the defect left by biopsy and an applicator for implanting the sponge into the biopsy site. The sponge is pre-cut to a diameter which approximately corresponds to the diameter of the punch which is used for excising a biopsy specimen. A fibrous cotton wad is attached to the other end of the applicator. After the specimen is excised the sponge is implanted into the space from which the specimen was taken. A slight pressure is applied to the sponge with the fibrous cotton wad for approximately 30 to 60 seconds to stop any excess bleeding.

9 Claims, 1 Drawing Sheet

BIOPSY WOUND CLOSURE DEVICE

This is a divisional of application Ser. No. 08/056,399 filed on May 4, 1993, U.S. Pat. No. 5,388,588.

BACKGROUND OF THE INVENTION

This invention relates to wound closure devices and more particularly to a biopsy wound closure apparatus and method for controlling bleeding and repair of the biopsy site during a routine skin biopsy procedure.

The skin is a complex anatomical system composed of two layers—the epidermis, or epithelium, which is visible to the naked eye, and the dermis or corium, below the epidermis which is firmly interlocked with the dermis. When the skin is punctured, the cells of the surrounding dermis and epidermis multiply to compensate for the loss of cells in the dermis and epidermis. Skin biopsies are frequently performed to diagnose abnormal skin conditions.

Surgical punches, ranging in diameter from 2 to 6 millimeters, are commonly used to excise small samples of skin for medical biopsies. The punches are razor sharp circular knives which are pressed against the skin and rotated to excise cylinder shaped samples for biopsies.

The current practice during a routine skin biopsy procedure is to use sutures, or for small wounds multiple butterfly bandages, to control the flow of blood and to repair the biopsy site. One deficiency with this practice is that some patients suffer anxiety during the suturing of wounds. Another deficiency is that a considerable amount of time is spent by physicians for hemostasis and repair of the biopsy site during routine biopsy procedures.

Sterile sponges have been used as packing material during surgery when hemostatic devices for controlling capillary, venous and arteriolar bleeding are either ineffective or Impractical. However, sterile sponges have neither been available nor used to repair biopsy sites or to control bleeding during biopsy procedures. Nor have small pre-cut implant devices having the same or similar diameters as surgical punches been used to repair resulting defects or to control bleeding after excisions of specimens for skin biopsies.

In view of the foregoing, it is apparent that a more efficient, effective, easy to use apparatus and method for performing a routine biopsy procedure would satisy an existing need.

SUMMARY OF THE INVENTION

The present invention satisfies the existing need by providing a pre-cut sterile sponge and applicator for hemostasis and repair of a biopsy site during a routine biopsy procedure.

The invention is comprised of a pre-cut sterile sponge of the approximate shape and size of a specimen which is excised during a skin biopsy procedure and an applicator for inserting the sponge. The closure apparatus and method are effective for controlling bleeding, promoting healing, and reduce the likelihood of excessive scarring.

The sterile sponge and applicator are contained within the interior of a transparent plastic tube. After a specimen has been excised, the sterile sponge is implanted into the wound with the applicator. This embodiment also permits the sponge to be diametrically pre-compressed.

The invention is comprised of a transparent cylindrical tube; a close fitting sterile sponge inside of said tube of about the same diameter as a small cylindrical punch for excising a skin biopsy specimen; an applicator inside of said tube for implanting the sponge into said biopsy site; and a fibrous cotton wad attached to one end of the applicator.

The foregoing features and benefits of our invention, together with other features and benefits, will be apparent from the ensuing detailed description taken in conjunction with the accompanying drawings. The best mode which is contemplated in practicing our invention is disclosed and the subject matter in which exclusive property rights are claimed is set forth in each of the numbered claims which are appended to the detailed description.

DETAILED DESCRIPTION OF THE PREFERRED EMBODIMENT

Figure 1:
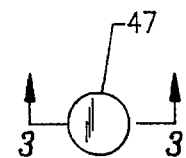
FIG. 1 is a plan view of an alternate embodiment in which a sterile sponge and applicator are stored in a transparent cylindrical tube.
Figure 4:
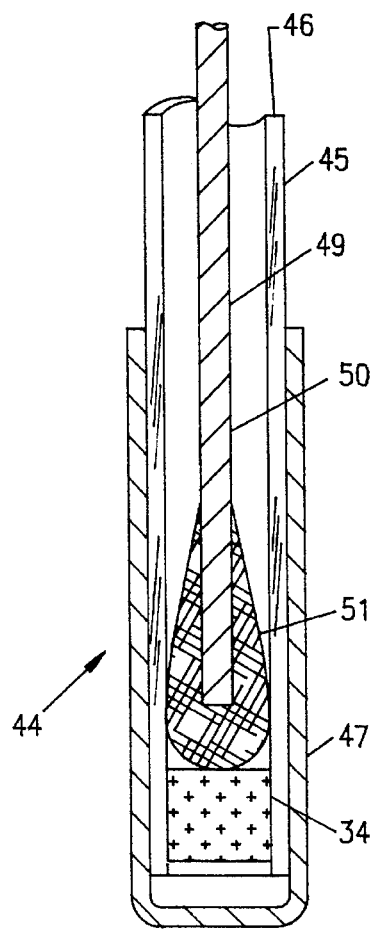
FIG. 4 is an enlarged fragmentary view of FIG. 3.
Figure 3:
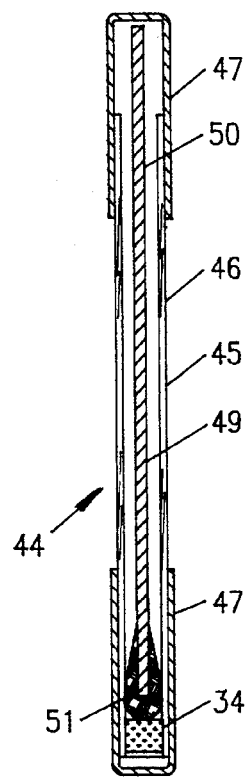
FIG. 3 is a cross-sectional view taken on the line 3—3 in FIG. 1.
Figure 2:
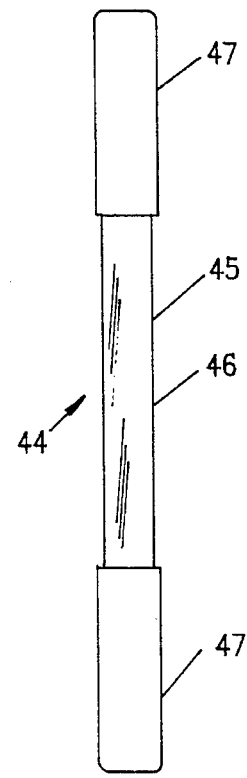
FIG. 2 is a front elevational view of the alternate embodiment shown in FIG. 1.

Referring now to the drawings wherein like numerals designate like and corresponding parts throughout the several views, in FIGS. 1 through 4, inclusive, is illustrated, for purposes of describing our invention, a closure device 44 for repair of resulting skin defect and controlling bleeding during a routine skin biopsy procedure with reduction of chances of inducing excessive scar tissue.

A sterile sponge 22 is pre-cut to diameters which correspond to diameters of conventional skin punches (not shown) by way of example, 2, 3, 4, 5 and 6 millimeters. The sponge 22 is a water-insoluble, porous item which is absorbed completely, with little tissue reaction. When the sponge 22 is implanted into the bleeding site, the sponge 22 absorbs blood, swells and terminates the flow of blood in the bleeding site and by filling up the biopsy site defect promotes healing without the necessity of approximation of the defect sides by suturing.

One material which has been evaluated and found to be acceptable for practicing our invention is an absorbable gelatin sponge manufactured by the Upjohn Company under the registered trademark "GELFOAM". It is a water-insoluble, off-white, non-elastic, porous, pliable product made from purified pork skin gelatin USP granules and is available in the form of pads.

The method for using our invention consists of the following steps. The biopsy area is cleaned and draped to provide a sterile environment. The skin is next anesthetized by an intradermal injection of a suitable anesthesiology material. A proper size sterile punch is pressed against the skin and rotated to excise specimens of epidermis and subcutaneous tissue for biopsy.

A third embodiment 44 of the invention is shown for purposes of illustrating the invention in FIGS. 1 through 4. The invention is comprised of a sterile container 45 having a cylindrical body 46 and a pair of identical cylindrical caps 47 at each end of the body 46, a closely fitting cylindrical sponge 34 in the interior of the body 46 and a plunger 49. The body 46 is preferably made of a transparent plastic material such that the sponge 34 is visible. The plunger 49 is comprised of a slender cylindrical rod 50 and a cotton fiber wad 51 at one end of the rod 50.

The sterile sponge 34 is located close to the end of the body 46 whereby when the end caps 47 are removed from the body 46, the sponge 34 can be implanted into the bleeding site by depressing the plunger 49. With this embodiment 44 pressure can be applied to the sponge 34 with the cotton fiber wad 51 to seal the wound by further depressing the plunger 49 to expose the cotton fiber wad 51. With this embodiment 44 the sponge 34 may also be diametrically pre-compressed in the cylindrical body 46.

From the foregoing it will be understood that our invention provides an improved closure device and method for performing a routine biopsy procedure. Moreover, it will be appreciated that our improved closure device provides numerous benefits, among which are, a reduction in cost and time, reduced handling of tissue, and a reduction in the likelihood of inducing the formation of excessive scar tissue.

Although but several embodiments of our invention have been illustrated and described, it is not our intention to limit our invention to these embodiments since other embodiments can be provided by substitutions in materials and modifications in the shape, number and arrangements of parts and steps in our closure device and changes in steps in our method without departing from the spirit thereof.

We claim:

1. A closure device for the repair of skin tissue, controlling bleeding, and reducing the likelihood of inducing excess scar tissue during a routine skin biopsy procedure, comprising: a cylindrical tube; a close fitting pre-formed cylindrical sponge in the interior of said cylindrical tube made from a foam material which swells and is absorbed in a biopsy site with little tissue reaction, said sponge being pre-formed to a diameter within a range of 2 to 6 millimeters which is approximately equal to the diameter of a circular blade of a punch used for taking a specimen of skin for a biopsy from said biopsy site; and an applicator for implanting said sterile sponge into said biopsy site after the excising of said specimen by said punch; and a fibrous cotton wad at an end of said applicator for pushing said sponge from said tube and applying pressure to said sponge for a short interval of time after said sponge has been implanted into said biopsy site.

2. The closure device recited in claim 1 wherein the diameter of said pre-formed cylindrical sponge is equal to the diameter of said circular blade of said punch.

3. The closure device recited in claim 1 wherein the diameter of said pre-formed cylindrical sponge is greater than the diameter of said circular blade of said punch.

4. The closure device recited in claim 1 wherein said sponge is a water-insoluble, non-elastic, porous and pliable product made from purified pork skin gelatin USP granules.

5. The closure device recited in claim 1, further comprising a cylindrical cap removably attached to each end portion of said cylindrical tube for enclosing said applicator and said cylindrical sponge.

6. The closure recited in claim 1 wherein said sponge is diametrically pre-compressed when said sponge is in said interior of said cylindrical tube.

7. A closure device for the repair of skin tissue, controlling bleeding, and reducing the likelihood of inducing excess scar tissue, during a routine skin biopsy procedure, comprising: a hollow transparent cylindrical tube; a close-fitting pre-formed cylindrical sponge in the interior of said tube which is about the same diameter as a diameter within a range of 2 to 6 millimeters of a circular blade of a punch used for excising a specimen of skin for a biopsy; and an applicator for pushing said sponge from said tube and implanting said sponge into a bleeding site caused by the excising of said specimen, said applicator having a rod, and having a fibrous cotton wad, said wad being attached to an opposite end portion of said rod.

8. A closure device for the repair of skin tissue, controlling bleeding, and reducing the likelihood of inducing excess scar tissue, during a routine skin biopsy procedure, comprising: a tubular body for receiving a close fitting sterile sponge in the interior of said body, a pre-cut cylindrical sponge in an interior of said body having a diameter which is about the same diameter as the diameter within a range of about 2 to 6 millimeters of a circular blade of a punch used for excising a specimen of skin for a biopsy; and an applicator for implanting the sponge into the bleeding site stored in said tubular body, said applicator being a slender plunger in the interior of said body for implanting said sponge into a bleeding site caused by the excising of a skin specimen for a biopsy, said plunger having a slender rod and a fibrous cotton wad attached to one end of said rod, said end with said cotton wad being adjacent to said cylindrical sponge, the other end portion of said rod extending outwardly from said tubular body for pushing said sponge from said tubular body and implanting said cylindrical sponge into said bleeding site; and a cylindrical cap removably attached to opposite end portions of said tubular body for enclosing said applicator and said cylindrical sponge.

9. The closure device recited in claim 8 wherein said tubular body is transparent.

* * * * *